US006657717B2

(12) United States Patent
Cadell et al.

(10) Patent No.: US 6,657,717 B2
(45) Date of Patent: Dec. 2, 2003

(54) DEVICE FOR VERIFYING THE ACCURACY OF A SPECTRAL ANALYZER

(75) Inventors: Theodore E. Cadell, Conestogo (CA); Paul Drennan, Waterloo (CA); James Samsoondar, Cambridge (CA); Romuald Pawluczyk, Waterloo (CA); Ashwani Kaushal, Mississauga (CA); Bronislaw Bednarz, Toronto (CA); John Kuta, Toronto (CA)

(73) Assignee: CME Telemetrix Inc., Waterloo (CA)

( * ) Notice: Subject to any disclaimer, the term of this patent is extended or adjusted under 35 U.S.C. 154(b) by 36 days.

(21) Appl. No.: 10/085,983

(22) Filed: Feb. 28, 2002

(65) Prior Publication Data

US 2002/0118361 A1 Aug. 29, 2002

Related U.S. Application Data

(63) Continuation of application No. PCT/CA00/01006, filed on Aug. 31, 2000.
(60) Provisional application No. 60/151,681, filed on Aug. 31, 1999.

(51) Int. Cl.[7] .................................................. G01J 4/10
(52) U.S. Cl. ...................... 356/243.1; 600/473; 356/41
(58) Field of Search ......................... 356/243.1, 243.2, 356/243.3, 243.4, 243.5, 243.6, 243.7, 243.8, 247, 248, 39, 40, 41, 42; 250/252.1; 128/633, 665

(56) References Cited

U.S. PATENT DOCUMENTS

| | | | | |
|---|---|---|---|---|
| 4,322,164 A | | 3/1982 | Shaw et al. .................. 356/243 |
| 4,650,327 A | * | 3/1987 | Ogi ........................ 356/243.1 |
| 4,796,633 A | * | 1/1989 | Zwirkoski ................... 600/332 |
| 4,823,167 A | * | 4/1989 | Manska et al. .......... 356/243.1 |
| 4,825,872 A | * | 5/1989 | Tan et al. .................... 600/344 |
| 4,971,062 A | * | 11/1990 | Hasebe et al. .............. 600/473 |
| 4,981,355 A | * | 1/1991 | Higgins .................... 356/243.1 |
| 5,035,243 A | * | 7/1991 | Muz ........................... 600/344 |
| 5,077,476 A | * | 12/1991 | Rosenthal ................... 250/341 |
| 5,166,517 A | | 11/1992 | Volgyesi .................. 250/252.1 |
| 5,218,966 A | * | 6/1993 | Yamasawa .................. 128/677 |
| 5,278,627 A | | 1/1994 | Aoyagi et al. ................. 356/41 |
| 5,311,865 A | * | 5/1994 | Mayeux ....................... 128/633 |
| 5,361,758 A | | 11/1994 | Hall et al. ................... 128/633 |
| 5,429,128 A | | 7/1995 | Cadell et al. ............... 128/633 |
| 5,436,455 A | * | 7/1995 | Rosenthal et al. ...... 250/339.12 |
| 5,574,283 A | * | 11/1996 | Quintana ................. 250/341.1 |
| 5,823,961 A | * | 10/1998 | Fields et al. ................. 600/434 |
| 6,041,247 A | * | 3/2000 | Weckstrom et al. ......... 600/323 |
| 6,172,743 B1 | * | 1/2001 | Kley et al. ..................... 356/39 |
| 6,195,158 B1 | * | 2/2001 | Cadell et al. |
| 6,526,309 B1 | * | 2/2003 | Chance ....................... 600/473 |

FOREIGN PATENT DOCUMENTS

| GB | 2 280 024 A | 1/1995 |
|---|---|---|
| WO | WO 93 13706 A | 7/1993 |

* cited by examiner

*Primary Examiner*—Frank G. Font
*Assistant Examiner*—Sang H. Nguyen
(74) *Attorney, Agent, or Firm*—Heslin Rothenberg Farley & Mesiti P.C.

(57) ABSTRACT

The present invention provides an artificial member (80, 210) which mimics the absorbance spectrum of a body part and includes the spectral components of blood analytes. The artificial member comprises a light scattering and reflecting material, and has a chamber portion comprising one or more chambers (90, 100, 220). The artificial member is configured to be reproducibly received in a measuring receptor which receptor is operatively connected to a non-invasive monitoring device.

28 Claims, 11 Drawing Sheets

DEVICE FOR VERIFYING THE ACCURACY OF A SPECTRAL ANALYZER

CROSS-REFERENCE TO RELATED APPLICATIONS

This application claims the priority of International Application No. PCT/CA00/01006 filed Aug. 31, 2000, which claims the priority of U.S. provisional application 60/151,681 filed Aug. 31, 1999, the disclosures of which are incorporated herein by reference in their entirety.

FIELD OF THE INVENTION

This invention is in the field of non-invasive spectral analysis of analytes in tissues and relates more particularly to a device which may be used with a non-invasive monitoring system used for determining concentrations of various blood components.

BACKGROUND OF THE INVENTION

Non-invasive devices exist which are used externally to measure either the concentration of the constituent in gases admitted by the body or the concentrations contained in a patient's body part, typically a finger. U.S. Pat. No. 5,429,128 describes a finger receptor which receives a finger of a user and is for use with a non-invasive monitoring device. U.S. Pat. No. 5,361,758 describes such a monitoring device.

During the course of using a monitoring device which is operatively coupled to a finger receptor, many uses of the receptor and the monitoring device will, with time, result in variations in readings due to internal drift and other variable aspects of such monitoring devices. Accordingly, it is desirable to have a means to rapidly and easily check the precision and accuracy of such a monitoring device.

SUMMARY OF THE INVENTION

The present inventors have developed a device shaped to fit a receptor which is operatively connected to a non-invasive monitoring device, which device is useful in monitoring the precision and accuracy of the non-invasive monitoring device and which permits photometric correction of the instrument.

In its broad aspect, the invention provides a method and a device made of materials for carrying out the method which reproduce absorption spectra associated with various body parts when such parts are subjected to spectral determination. A device according to the present invention is made of a material that exhibits the same light scattering and absorbance characteristics as a body part, preferably of an earlobe, lip, fold of skin or finger, most preferably, a finger.

According to one embodiment of the present invention, there is provided an artificial member, which mimics the absorbance spectrum of a body part and includes the spectral components of blood analytes comprising a light scattering and reflecting material, which member has a chamber portion comprising one or more chambers, said member configured to be reproducibly received in a measuring receptor which receptor is operatively connected to a non-invasive monitoring device, preferably the body part which is mimicked is a finger. In one embodiment there is one chamber, while in another there are two chambers.

In another embodiment, each chamber is filled with an O-cellulose material which mimics light scattering properties of tissue, preferably each chamber is filled with a gel material containing Amaranth and sodium benzoate and holding light scattering and reflective particles which mimic the light scattering properties of tissue. In another embodiment, the material which fills each chamber is fluid free. In yet another embodiment, the reflective particles comprise Teflon-PTFE, Titanium Dioxide ($TiO_2$) or are Polystyrene nanospheres.

In yet another embodiment, the light scattering and reflecting material of the member is Teflon-PTFE, preferably the configuration of the member where in the configuration of the member to be reproducibly received, comprises a stabilizing member extending from the chamber portion to reversibly urge other surfaces of the member into contact with the measuring receptor, preferably the stabilizing member is as depicted in FIG. 9.

In another aspect according the present invention, there is provided a method of transferring algorithms from one spectral instrument to another comprising the steps of:
measuring a spectral response of a member in a first spectral instrument;
measuring a spectral response of the member in a second spectral instrument; determining any difference in measurements from the first instrument and second instrument; and
modifying the algorithms of the instruments to account for any difference, wherein the member of the method mimics the absorbance spectrum of a body part and includes the spectral components of blood analytes comprising a light scattering and reflecting material, which member has a chamber portion comprising one or more chambers, said member configured to be reproducibly received in a measuring receptor, which receptor is operatively connected to a non-invasive monitoring device, preferably the body part which is mimicked is a finger. In one embodiment of the method, there is one chamber, while in another there are two chambers.

In another embodiment of the method, each chamber is filled with an O-cellulose material which mimics slight scattering properties of tissue, preferably each chamber is filled with a gel material containing Amaranth and sodium benzoate and holding light scattering and reflective particles which mimic the light scattering properties of tissue. In another embodiment, the material which fills each chamber is fluid free. In yet another embodiment, the reflective particles comprise Teflon-PTFE, Titanium Dioxide ($TiO_2$) or are Polystyrene nanospheres.

In yet another embodiment of the method, the light scattering and reflecting material of the member is Teflon-PTFE, preferably the configuration of the member wherein the configuration of the member to be reproducibly received, comprises a stabilizing member extending from the chamber portion to reversibly urge other surfaces of the member into contact with the measuring receptor, preferably the stabilizing member is as depicted in FIG. 9.

The invention in another embodiment provides a method for mimicking the absorbance spectrum of a body part which includes the spectral components of blood analytes. The method comprises inserting a member in a measuring device which is operatively connected to a non-invasive monitoring device; taking measurements with the device and comparing the results with those obtained from a body part of subject which the member is intended to mimic, wherein the member is comprised of a light scattering and reflecting material, which member has a chamber portion comprising one or more chambers, and the member is configured to be reproducibly received in the measuring receptor.

According to one embodiment of this method, the member of the method mimics the absorbance spectrum of a body part and includes the spectral components of blood analytes comprising a light scattering and reflecting material, which member has a chamber portion comprising one or more chambers, said member configured to be reproducibly received in a measuring receptor which receptor is operatively connected to a non-invasive monitoring device, preferably the body part which is mimicked is a finger. In one embodiment of the method, there is one chamber, while in another there are two chambers.

In another embodiment of the method, each chamber is filled with an O-cellulose material which mimics light scattering properties of tissue, preferably each chamber is filled with a gel material containing Amaranth and sodium benzoate and holding light scattering and reflective particles which mimic the light scattering properties of tissue. In another embodiment, the material which fills each chamber is fluid free. In yet another embodiment, the reflective particles comprise Teflon-PTFE, Titanium Dioxide ($TiO_2$) or are Polystyrene nanospheres.

In yet another embodiment of the method, the light scattering and reflecting material of the member is Teflon-PTFE, preferably the configuration of the member wherein the configuration of the member to be reproducibly received, comprises a stabilizing member extending from the chamber portion to reversibly urge other surfaces of the member into contact with the measuring receptor, preferably the stabilizing member is as depicted in FIG. 9.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

As used herein "concentration" or "concentration level" means the amount or quantity of a constituent in a solution whether the solution is in vitro or in vivo.

As used herein, "constituent" means a substance, or analyte found in a tissue and includes carbohydrates such as, for example, glucose, bilirubin, a protein, for example, albumin or hemoglobin.

As used herein, "fluid free" means having no appreciable amount of liquid present.

As used herein, "tissue" means any tissue of the body of a subject including, for example, blood, extracellular spaces, and can mean the entire composition of a body part such as a finger or ear lobe.

As used herein, "subject" means any member of the animal kingdom including, preferably, humans.

As stated above, the present inventors have prepared a device which is capable of insertion in a receptor which is used with a non-invasive monitoring device. The use of such a device or artificial member is to enable the user of such a non-invasive monitoring device to quickly and easily check the precision and accuracy of the non-invasive monitoring device.

Figure 1:
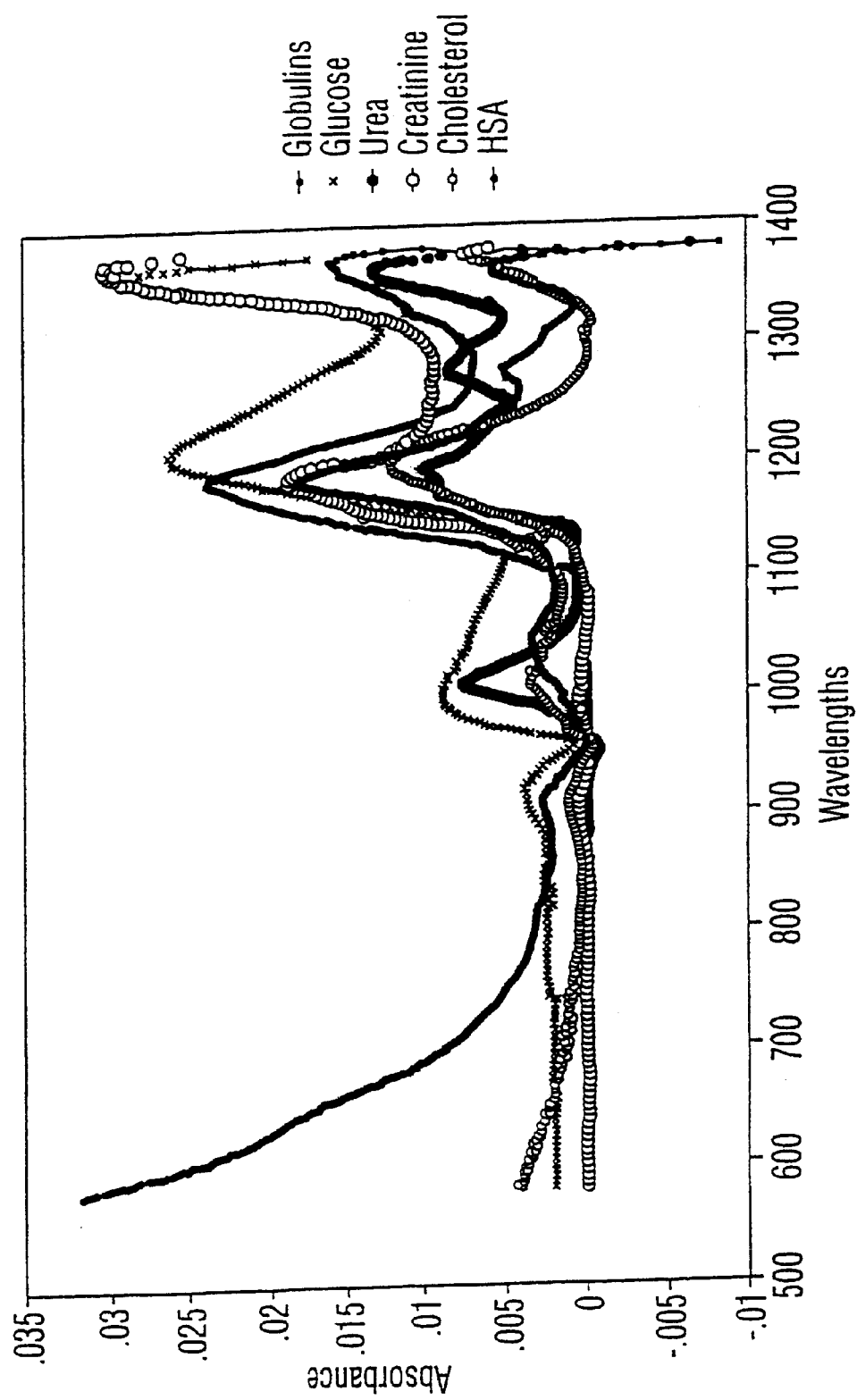
FIG. 1 shows absorbance spectra from 500–1380 nm for globulins, glucose, urea, creatinine, cholesterol and human serum albumin with water displacement compensation.
Figure 2:
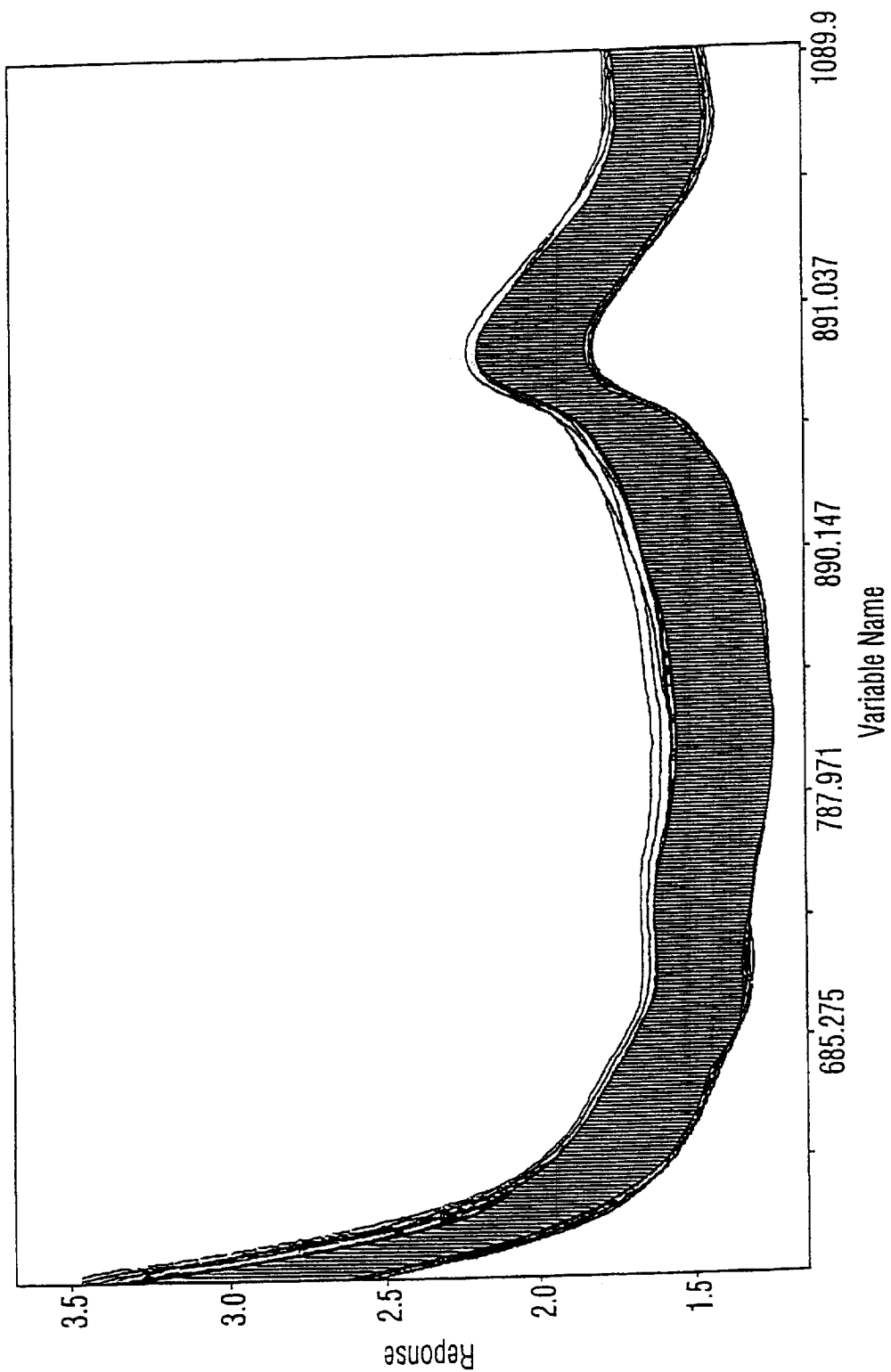
FIG. 2 shows 2013 absorbance spectra from 585–1100 nm for the finger from 32 subjects.

Spectral data, obtained using a standard spectrophotometer and compensated for water displacement, were collected from in vitro measurement of a cuvette containing samples of various blood constituents and are illustrated in FIG. 1. As may be seen, the spectra associated with the various constituents are complex. In contrast, the spectra for a living finger is relatively simple, particularly in the 500–1100 nm region. This may be seen in FIG. 2. Measurements taken in this region are relatively consistent regardless of individual measurements or the individual being scanned. In this respect, the data presented in FIG. 2 represent the combined spectra of 33 people for whom a total of 2,013 measurements were taken and are collectively presented. Accordingly, an artificial member must be able to provide a spectrum which is comparable to those presented in FIG. 2 or the absorbance spectra of another body part. It will be appreciated that in order to develop a comparable artificial member, such member must mimic the situation of which light is directed to a body part. Light entering the body is scattered and that light which emerges radiates in virtually every direction. Absorption begins at the point of which the light enters the tissue. In the case of transmission, as the light passes through the tissue, more and more light is absorbed as the path length increases. Clearly, if path length is too great, very little light is left for measurement and the absorbance calculations will be subject to considerable error due to noise. The considerations are also true in respect of the artificial member. Consequently, according to one embodiment of the present invention, it is the artificial member that will exhibit the same properties of light scattering, reflectivity and absorption as exhibited by a living human finger. Accordingly, an artificial member of the present invention is made of a highly reflective material such as, for example, teflon, in particular, teflon-PTFE virgin material (where PTFE means polytetrafluoroethylene). In addition, to concurrently mimic scatter, which is derived from the interior of a living body part, the artificial member must show sufficient internal reflectance to achieve a comparable result. In this respect, a chamber, or container space exists in the member, although, depending on the body part being mimicked, reflective material may comprise part of the internal structure of the chamber of the member.

An artificial member must be capable of being easily inserted into and removed from a receptor which is used to measure spectral characteristics of constituents in a body part. In this respect, the shape of the artificial member will be determined by the shape of the receptor. In the case of a finger receptor, the artificial member must have corresponding shapes to ensure that there is a constant path length from the point at which light is delivered to the finger or artificial finger and the point at which light exits the finger or artificial body part.

It will be appreciated by those skilled in the art that an artificial member of the present invention is for use in association with any measuring receptor which is combined with any non-invasive monitoring device which is based on the principle of measuring the absorbance (or reflectance) of radiation passing through (or reflecting from) a body part. In this respect, such devices operate according to the Beer-Lambert Law, namely, that the concentration of constituents is proportional to a constant of proportionality (the extinction coefficient), the path length, and the absorbance (LOG 10[1/T], where T is the transmittance, i.e., the proportion of light of a given wavelength that is transmitted through the matrix).

By measuring the absorbance at a number of predetermined wavelengths, some of which will control for path length, it is possible to calculate the concentration of a given constituent. The same principles of measurement which are applied to determining concentration of constituents in body parts with a non-invasive device are equally applicable to an artificial member of the present invention. Consequently, while water is a preferred constituent for measurement and accuracy testing with an artificial member, any other constituent, or constituents may be used. In this respect, it will be appreciated that the constituents will be preferably held in the member, preferably in the chamber or chambers of the member. In some applications, it may be necessary to introduce other absorbing or reflecting material in the chamber or intermixed with the composition of the reflective material.

It should noted that there are several ways in which absorbance measurements may be taken, and without limiting the scope of the applicability of the present invention, the two methods are: (1) use light from a scanning monochromator and pass it through a selected part of the body and collect the light transmitted through onto a silicon detector. A second measurement involves a measurement of the light transmitted in the absence of the body part. From these two measurements the transmittance, and hence the absorbance, may be calculated; (2) use a polychromatic light source, pass it through the body part to be measured, collect the light, collimate it onto a diffraction grating and focus the different wavelengths of light on a linear array detector. Each element of the array will then measure the intensity of light for a narrow band of wavelengths. A similar measurement in the absence of the body part (reference scan) will then allow computation of the transmittance for each element. Because the various elements of the array have slightly different dark leakage currents, it is necessary to record a dark current and subtract it from both the sample scan and the reference scan before calculation of transmittance and absorbance.+

There are several typical parts of the body from which measurements are made and these include the finger, the lip, the earlobe, a pinch of skin at the waist, the web between the thumb and forefinger, the web between toes. Accordingly, the present invention includes artificial members replicating each of these.

One of the problems encountered in measuring absorbance in tissue is the spectral variability from one instrument to another due to physical differences in light transmission and collection. Because the phantom finger is designed to minimize variability of spectral response and physical placement in the finger receptor, it can be used to quantify the spectral differences between instruments. With careful wavelength calibration, the difference in spectral response of the phantom finger between one instrument and another may be used to correct the spectrum of the second instrument to that of the first by adding the spectral difference to the second instrument. This is termed photometric correction and coupled with suitable wavelength accuracy, is the basis on which algorithms can be transferred from one instrument to another.

DESCRIPTION OF EXEMPLARY EMBODIMENTS

Figure 12:
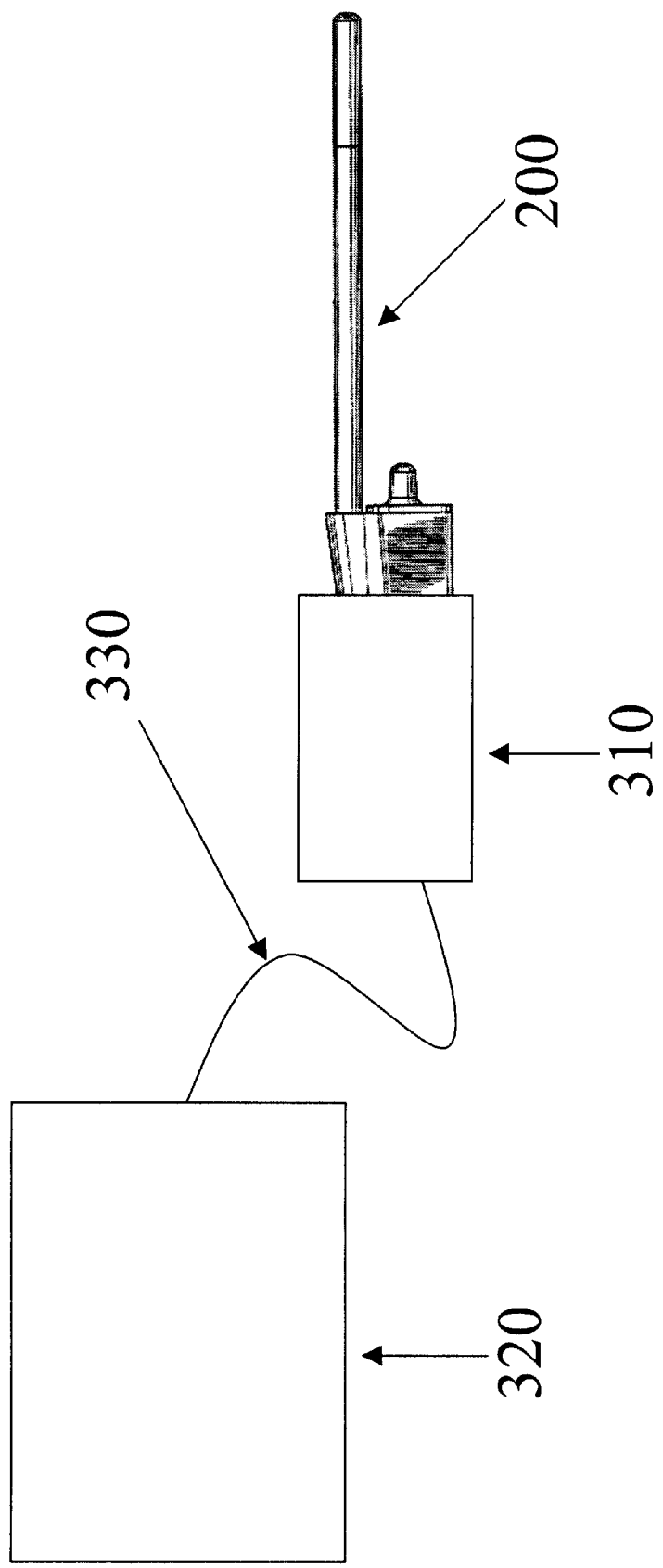
FIG. 12 shows an artificial finger according to the present invention used in association with a finger receptor, which is operatively connected to a non-invasive monitoring device.

We will now describe two non-limiting exemplary embodiments of the present invention. Firstly, referring to FIGS. 7 and 8, an artificial member according to the present invention is illustrated. In particular, the artificial member is intended to represent an artificial finger 200 for use in association with a finger receptor 310, which is operatively connected (via 330) to a non-invasive monitoring device 320 such as a spectrophotometer, as shown in FIG. 12.

Figure 7:
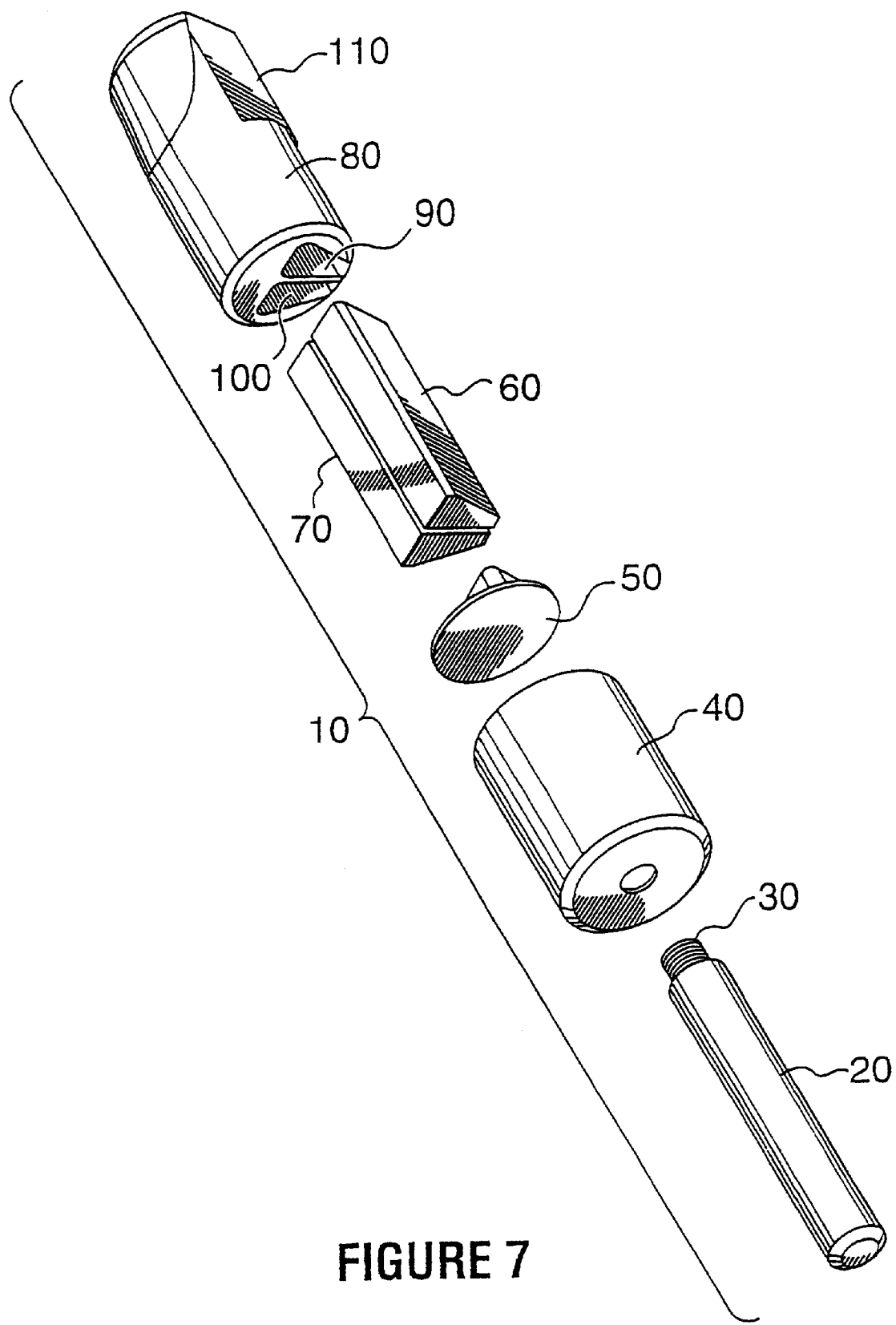
FIG. 7 is an isometric exploded view of an artificial member according to the present invention in a configuration for use with a finger receptor.
Figure 8:
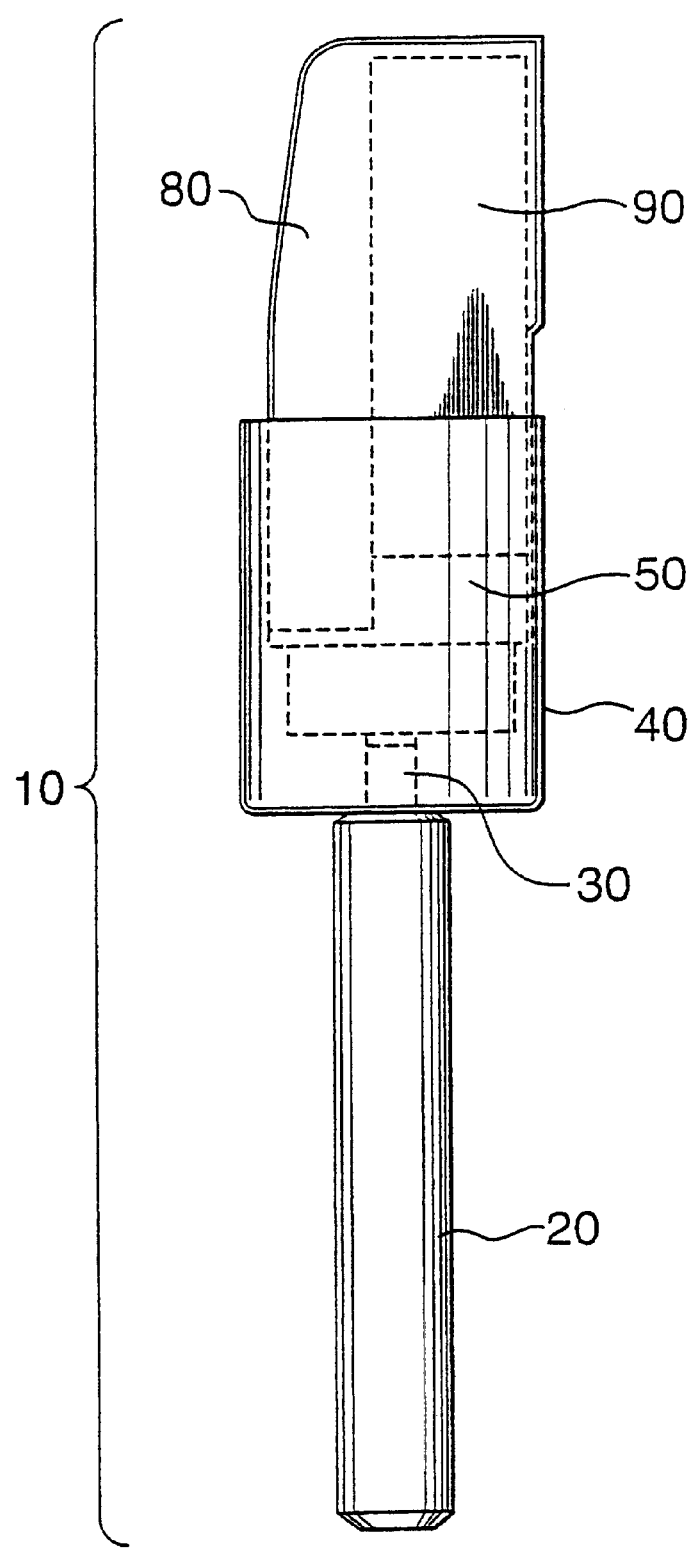
FIG. 8 is a side view of the member of FIG. 7.

The artificial finger 10 is comprised of a handle which may be prepared from aluminum or any other material which is rigid and has strength characteristics. The handle at 20 has a tip 30 which is used to connect the handle with a holding collar 40. The holding collar is used to provide a large grasping means as well as sealing cover for the highly reflective and light scattering portion of the artificial finger 80. The holding collar 40 is made of black plastic (DELRIN); however, any other minimally reflective or nonreflective plastic material is acceptable. The holding collar fits by means of an interference fit over the artificial member 80. The artificial member 80 is comprised of a material which provides a scattering effect similar to tissue such as the skin or a digit, namely Teflon-PTFE; however, any other material such as Fluorosint™ (DSM Engineering Plastic Products, Inc.) or Teflon-PTFE with 25% glass fibers which is capable of providing such scattering effect is suitable. This member has a hollow or chamber-like portion which determines the amount of internal scattering based on the material filling the cavity. The exact dimensions of this chamber are selected to achieve a spectrum of absorption similar to that observed of a natural finger. More than one chamber may be used. According to a preferred embodiment to the chamber as shown in FIG. 7 is divided into two portions, 90 and 100, although similar results may be achieved with more chambers. The chambers 90 and 100 act as containers to hold water or any other solutions which are being used as part of the artificial member. Also placed in the artificial member for the purposes of replicating absorbance of a finger are O-cello materials commonly available as sponge 60, 70 (SCOTCH BRIGHT™) and which are shaped to fit into the containers 90 or 100. The chamber may also be filled with gel materials which hold light scattering materials such as Titanium Dioxide (TiO$_2$) or Polystyrene nanospheres.

A stopper 50 made of rubber or other suitable material is fashioned to fit in to seal the top open end of containers 90 and 100 over which holder collar 40 is placed. These parts and their interrelationship is better seen in FIG. 8 which provides a side view of the artificial finger and illustrates the components in place. The shaping of the artificial finger in order to provide an interface between the artificial member and the receptor thereby achieving a minimum of variability and maximum of repeatability whilst allowing for the passage of light through the artificial member thereby optimizing pathlength and its variability between measurements with the artificial member is seen in the isometric exploded view in FIG. 7 as item 110. This shaping will vary from one artificial member to the other depending upon the receptor for which the artificial members created and depending upon the device in which the artificial member is being used to verify the accuracy of the spectral analyzer.

Figure 9:
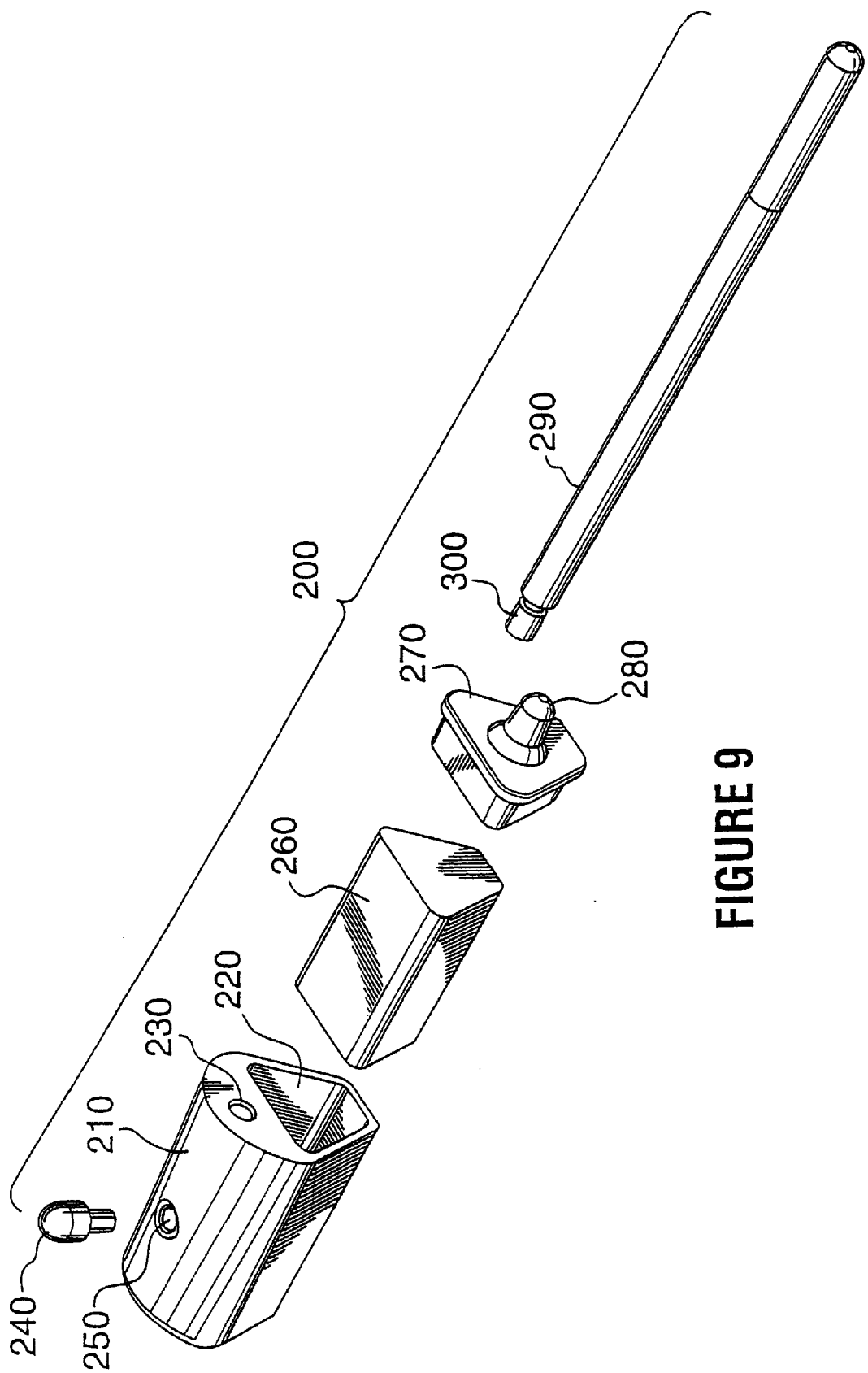
FIG. 9 is an isometric exploded view of a further embodiment of an artificial member according to the present invention in a configuration for use with a finger receptor.
Figure 10:
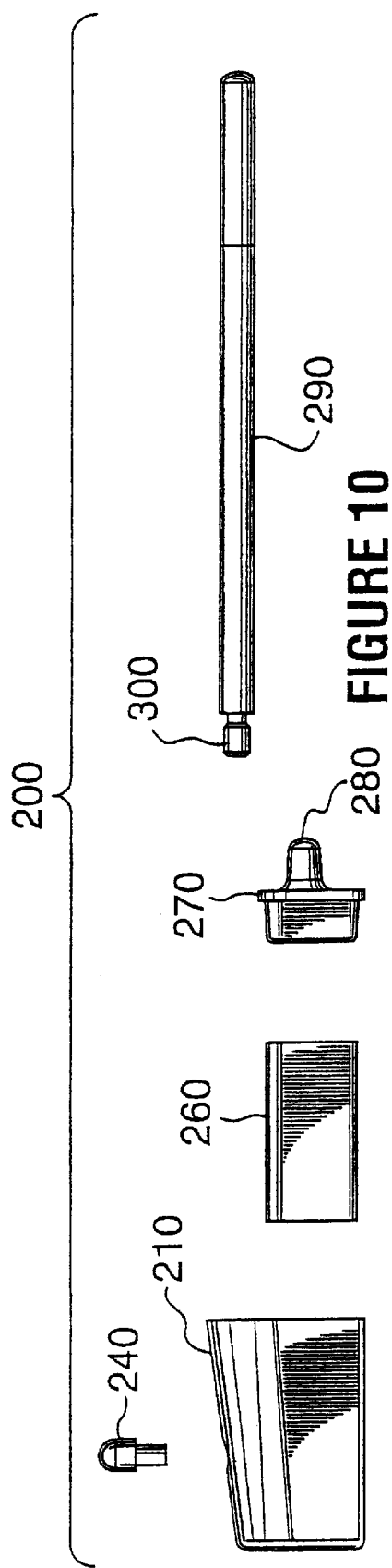
FIG. 10 is a side view of the member of FIG. 9.
Figure 11:
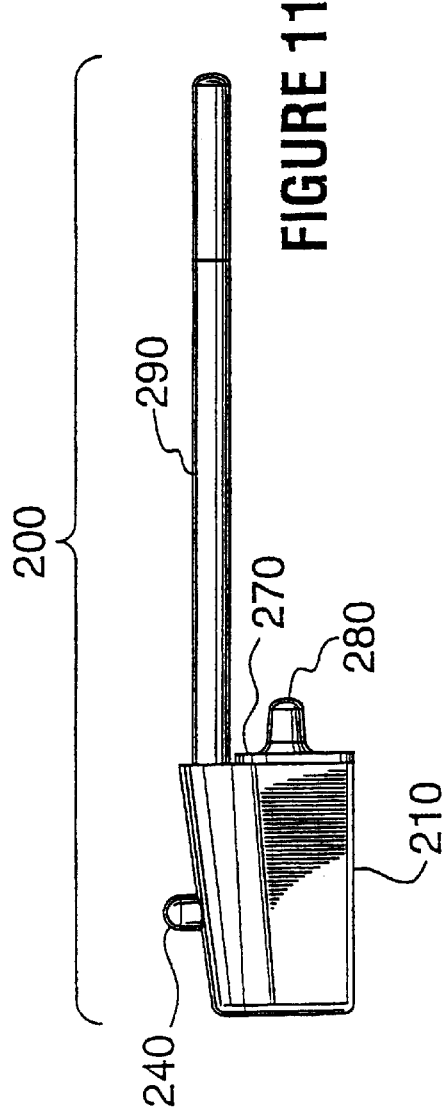
FIG. 11 is a side view of an assembled member of FIGS. 9 and 10.

Referring now to FIGS. 9, 10, and 11, another embodiment of an artificial member according to the present invention is illustrated. In particular, this artificial member is also intended to represent an artificial finger for use in association with a finger receptor which is operatively connected to a non-invasive monitoring device such as a spectrophotometer.

The artificial finger 200 of FIGS. 9, 10, and 11 is comprised of a handle, which may be prepared from aluminum or any other material, which is rigid and has strength characteristics. The handle at 290 has a tip 300, which is used to connect the handle to the artificial member 210 at 230. The artificial member is comprised of a material which provides a scattering effect similar to tissue such as the skin or a digit, namely, Teflon-PTFE; however, any other material such as Fluorosint™ or Teflon-PTFE with 25% glass fibers which is capable of providing such a scattering effect is suitable. This member has a hollow or chamber-like portion 220, which determines the amount of internal scattering based on the material filling the cavity. The exact dimensions of this chamber are selected to achieve a spectrum of absorption similar to that observed of a natural finger. More than one chamber may be used. The chamber 220 acts as a container to hold water or any other solutions which are being used as part of the artificial member 210. Also placed in the artificial member for the purposes of replicating absorbance of a finger are O-cello materials commonly available as sponge 260 (SCOTCH BRIGHT™) and which is shaped to fit into the container 220. The chamber 220 may also be filled with gel materials, which hold light scattering materials such a Titanium Dioxide (TiO$_2$) or Polystyrene nanospheres. A stopper 270 made of rubber or other suitable material is fashioned to fit in to seal the top open end of the chamber 220. The stopper 270 may be inserted or removed by gripping the stub 280 provided for this purpose. A plunger, or "stabilizing member" 240 made of 303 Stainless Steel or other material which is rigid and has strength characteristics is press fit into the top of the artificial member into mating cavity 250 and is held in place by an interference fit between the two parts. The purpose of the interlocking plunger 240 is to provide exact placement and holding of the artificial member when inserted into a finger receptor which is operatively connected to a non-invasive monitoring device. The stabilizing member 240, when the artificial member is inserted into the finger receptor mates, with a corresponding hole precisely placed in the finger receptor for this purpose, resulting in accurate placement of the artificial member 210 each time it is inserted into the finger receptor. These parts and their interrelationship is better seen in FIG. 11 which provides a side view of the artificial finger and illustrates the components in place.

The following non-limiting examples are illustrative of the present invention.

EXAMPLES

Example 1

Figure 3:
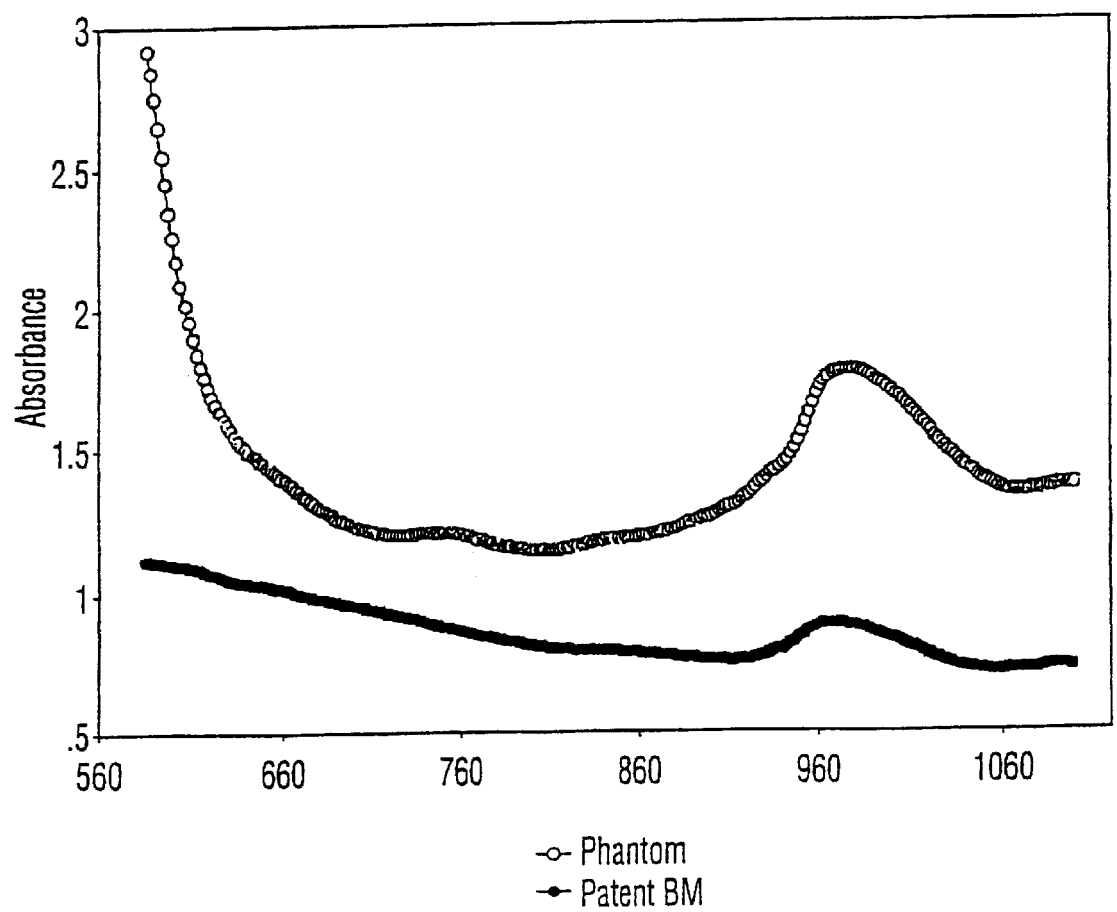
FIG. 3 shows absorbance spectra (580–1100 nm) for water in a subject's finger and an artificial member of the present invention.
Figure 4:
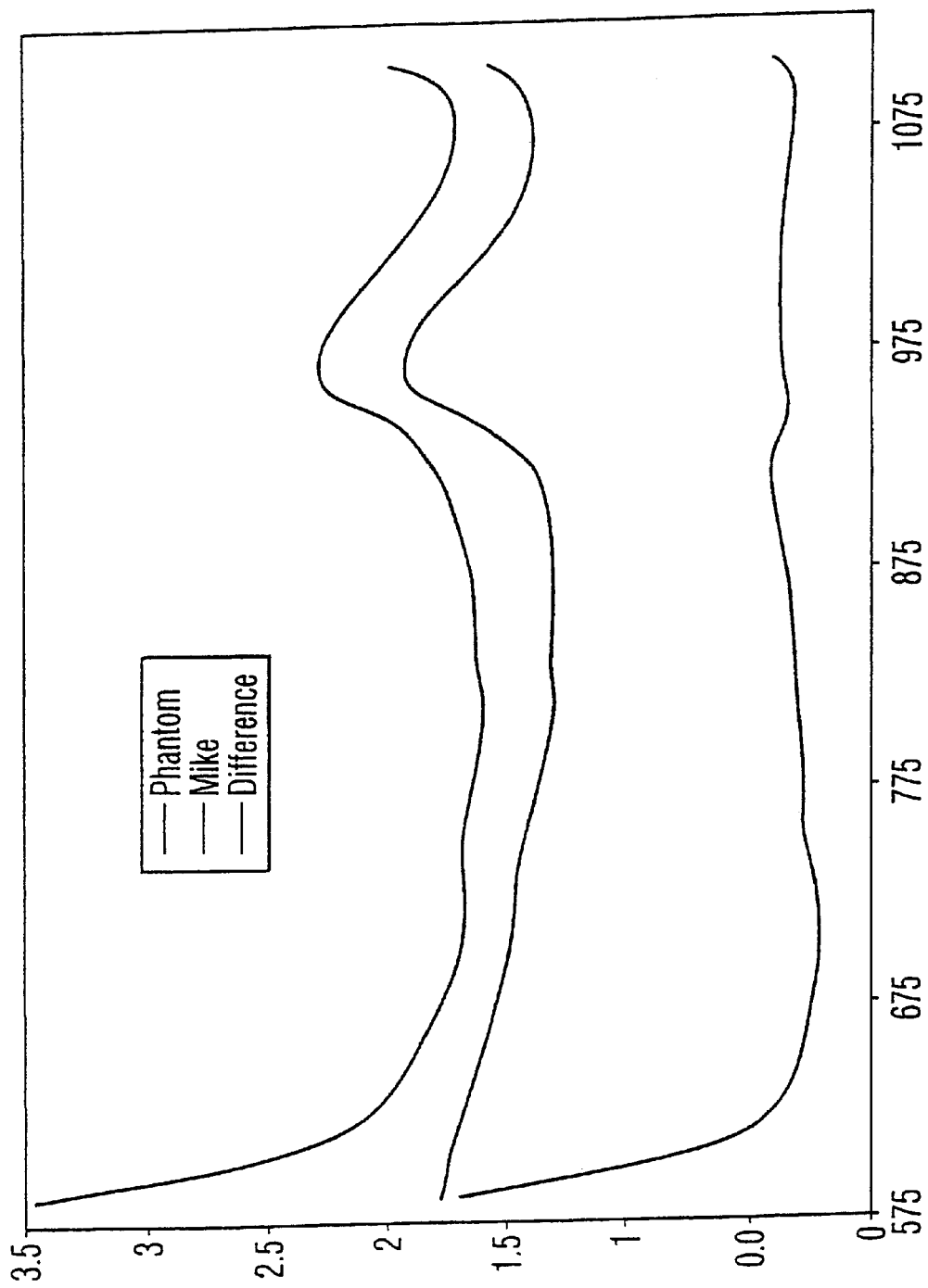
FIG. 4 shows absorbance spectra from 580–1100 nm for a subject's finger and an artificial member as shown in FIG. 3, as well as the curve representing difference of the first two spectra.
Figure 5:
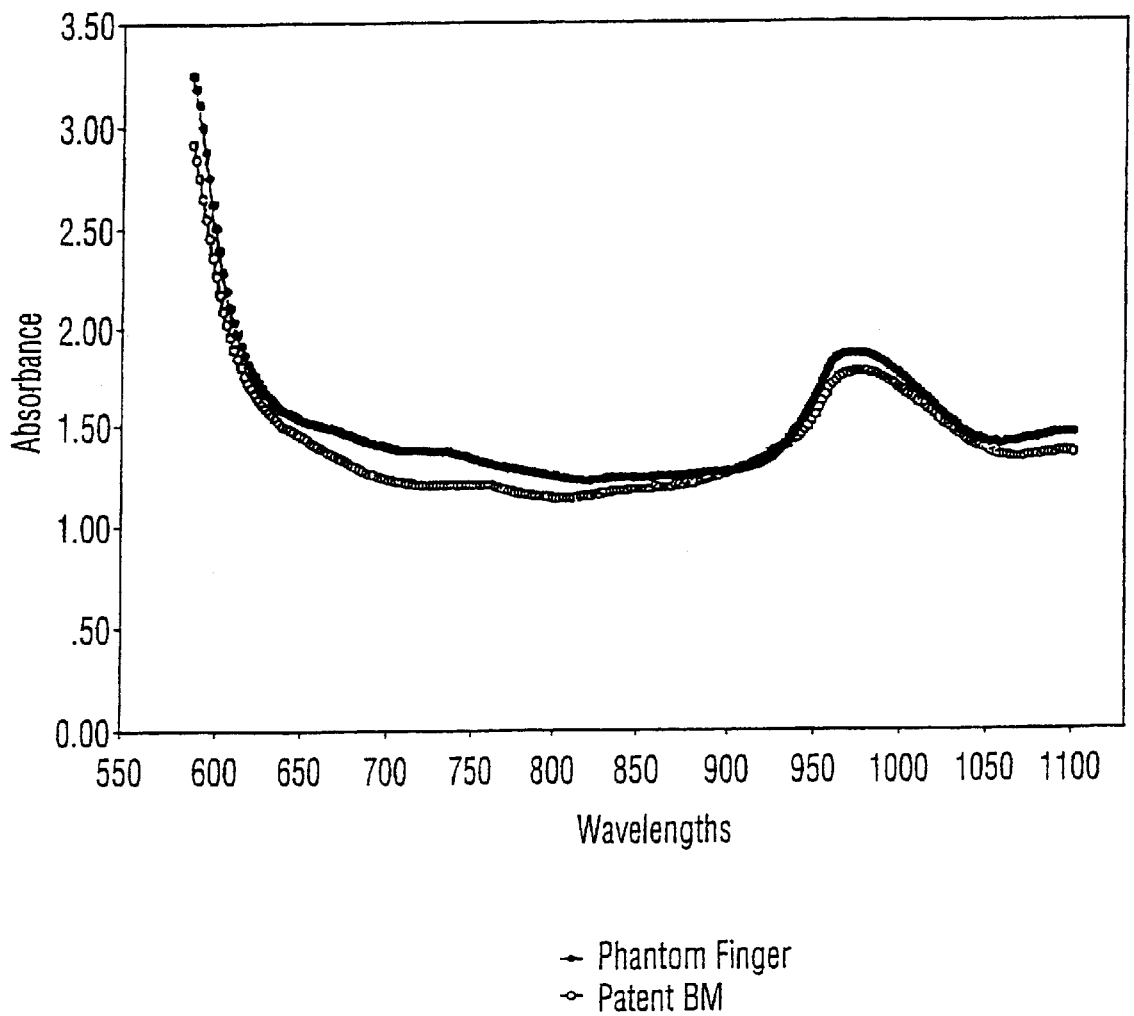
FIG. 5 is absorbance spectra from 580–1100 nm for water in a finger and in an artificial member of the invention where the member contains pink sponge (SCOTCH BRIGHT™) and water.

An artificial finger made of Teflon-PTFE was prepared, although as just stated, any other highly reflective and light scattering material can be used. The artificial finger has a hollow portion containing within a further reflective surface, also made of Teflon-PTFE. When filled with water, the artificial finger provides a spectrum somewhat similar to that observed in a normal finger (see FIG. 3). However, the peak of high absorbance found in the 580 nm region for a normal finger is noticeably missing. Indeed, the different aspects of the artificial finger and a normal finger are illustrated in FIG. 4. As may be seen, the only significant difference resides in the portion of the spectrum peak in the 580 nm region. To overcome the deficiency of the absorption spectra, various materials were tried; however, the inventors have determined that sponge pads (e.g., SCOTCH BRIGHT™) or other similar material is capable of providing an absorption spectrum like that of Amaranth which is comparable to absorption in a normal human finger. This may be seen most clearly in FIG. 5. This artificial finger can be used to check the performance of any non-invasive monitoring device which is used to monitor the concentrations of various components of a subject's body parts.

Example 2

An artificial finger made of Teflon-PTFE was prepared, although as just stated, any other highly reflective and light scattering material can be used. The artificial finger has a hollow portion containing within a further reflective surface, also made of Teflon-PTFE. When filled with water, the artificial finger provides a spectrum somewhat similar to that observed in a normal finger (see FIG. 3). However, the peak of high absorbance found in the 580 nm region for a normal finger is noticeably missing. Indeed, the different aspects of the artificial finger and a normal finger are illustrated in FIG. 4. As may be seen, the only significant difference resides in the portion of the spectrum peak in the 580 nm region. To overcome the deficiency of the absorption spectra, various materials were tried; however, the inventors have determined that sponge pads, (e.g., SCOTCH BRIGHT™) or other similar material, is capable of providing an absorption spectrum like that of Amaranth which is comparable to absorption in a normal human finger. This may be seen most clearly in FIG. 5.

Figure 6:
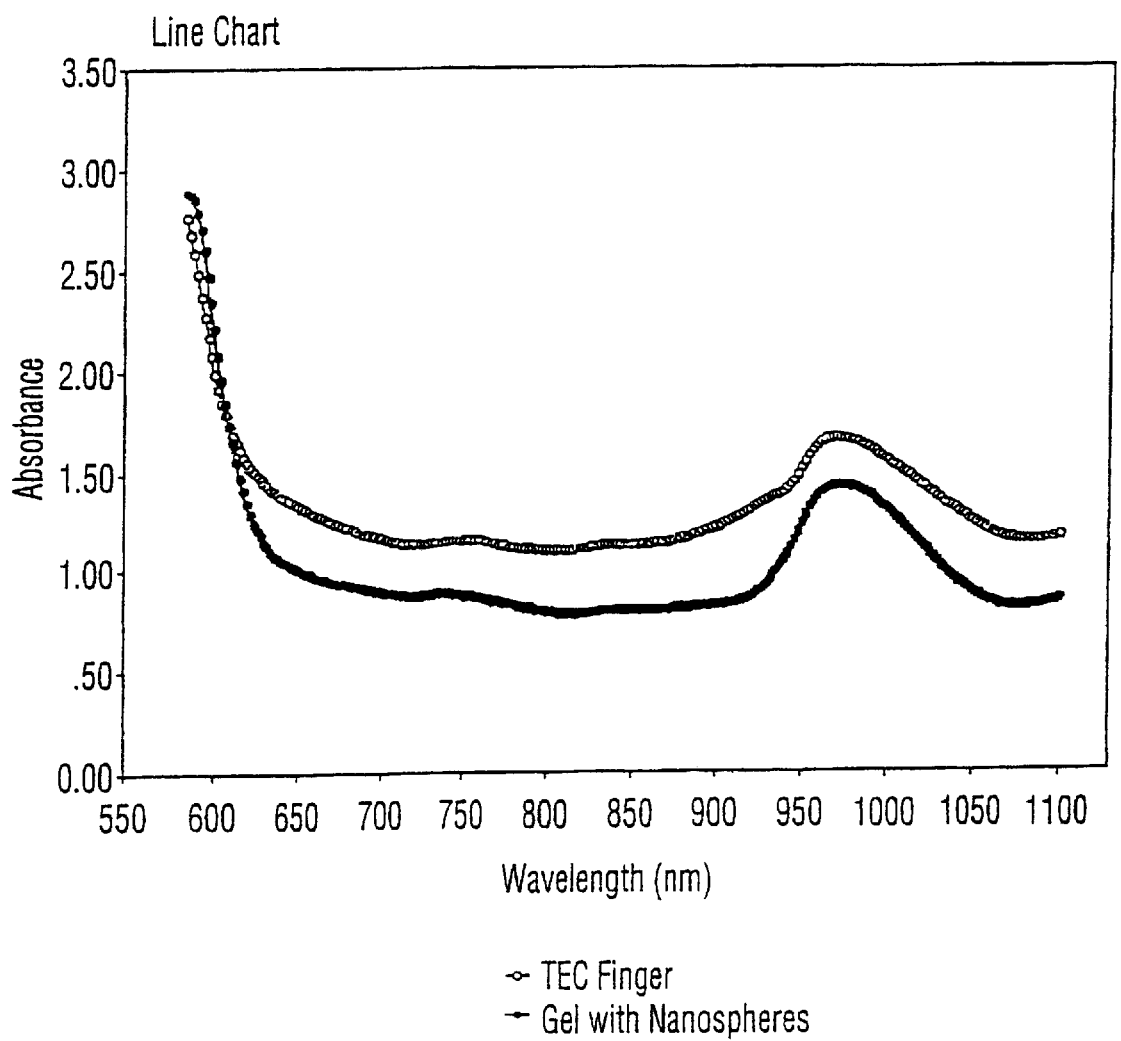
FIG. 6 is absorbance spectra from 580–1100 nm for water in a finger and in an artificial member of the invention where the member contains Polystyrene nanospheres in water and gelatin plus Amaranth and sodium benzoate as a preservative.

An artificial finger made of Teflon-PTFE was prepared and, as just stated, any other highly reflective and light scattering material can be used. The artificial finger has a hollow portion containing within a further reflective surface, also made of Teflon-PTFE. As just described, when filled with water, the artificial finger provides a spectrum somewhat similar to that observed in a normal finger, and the only significant difference resides in the portion of the spectrum peak in the 580 nm region. To overcome the deficiency of the absorption spectra, nanospheres of polystyrene in water and gelatin plus Amaranth and sodium benzoate as a preservative were used. The results are illustrated in FIG. 6.

As is readily apparent from the foregoing, this artificial finger can be used to check the performance of any non-invasive monitoring device which is used to monitor the concentrations of various components of a subject's body parts.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

All publications, patents and patent applications referred to herein are incorporated by reference in their entirety to the same extent as if each individual publication, patent or patent application was specifically and individually indicated to be incorporated by reference in its entirety.

What is claimed is:

1. An artificial member comprising:
    a) a housing defining a first and a second end, the housing having a solid wall, the solid wall defining one, or more than one chamber, the solid wall made of a light-scattering and light-reflecting material, the housing configured in the shape of a body part, the light-scattering and light-reflecting material approximating the light-scattering and light-absorbing characteristics of the body part, wherein the first and the second end are sealed.

2. The artificial member according to claim 1 wherein the body part is selected from the group consisting of a finger, a lip, an earlobe, a pinch of skin, a web of a hand, and a web between toes.

3. The artificial member according to claim 1, wherein the solid wall of the housing defines one chamber.

4. The artificial member according to claim 1, wherein the solid wall of the housing defines two chambers.

5. The artificial member according to claim 1, wherein the one, or more than one chamber is filled with an O-cellulose material.

6. The artificial member according to claim 1, wherein the one or more than one chamber is filled with a gel material containing Amaranth, sodium benzoate and light scattering and reflective particles.

7. The artificial member according to claim 6 wherein the light scattering and reflective particles comprise Teflon®-polytetrafluoroethylene (PTFE), Titanium Dioxide (TiO$_2$) Polystyrene nanospheres, or a combination thereof.

8. The artificial member according to claim 1 wherein the light-scattering and light-reflecting material is selected from the group consisting of Teflon® Teflon®-PTFE, Teflon®-PTFE with 25% glass fibers, and Fluorosint™.

9. The artificial member according to claim 1, further comprising a stabilizing member extending from the outer portion to reversibly urge the artificial member into contact with a measuring receptor.

10. A method for verifying the precision and accuracy of a non-invasive monitoring device comprising:
    a) inserting an artificial member into a measuring receptor, the measuring receptor operatively connected to the non-invasive monitoring device, the artificial member comprising a housing defining a first and a second end, the housing having a solid wall, the solid wall defining one, or more than one chamber, the solid wall made of a light-scattering and light-reflecting material, the housing configured in the shape of a body part, the light-scattering and light-reflecting material approximating the light-scattering and light-absorbing characteristics of the body part, wherein the first and the second end are sealed;
    b) measuring the absorbance spectrum of the artificial member; and
    c) comparing the absorbance spectrum of the artificial member with an absorbance spectrum obtained from the body part, thereby verifying the precision and accuracy of the non-invasive monitoring device.

11. The method according to claim 10, wherein the body part is selected from the group consisting of a finger, a lip, an earlobe, a pinch of skin, a web of a hand, and a web between toes.

12. The method according to claim 10, wherein the solid wall of the housing defines one chamber.

13. The method according to claim 10, wherein the solid wall of the housing defines two chambers.

14. The method according to claim 10, wherein the one, or more than one chamber is filled with an O-cellulose material.

15. The method according to claim 10, wherein the one, or more than one chamber is filled with a gel material containing Amaranth, sodium benzoate and light scattering and reflective particles.

16. The method according to claim 15, wherein the reflective particles comprise Teflon®-PTFE, Titanium Dioxide (TiO$_2$) Polystyrene nanospheres, or a combination thereof.

17. The method according to claim 10, wherein the light-scattering and light-reflecting material is selected from the group consisting of Teflon®, Teflon®-PTFE, Teflon®-PTFE with 25% glass fibers, and Fluorosint™.

18. The method according to claim 10, wherein the artificial member further comprises a stabilizing member extending from the outer portion to reversibly urge the artificial member into contact with the measuring receptor.

19. An artificial member comprising:
    a) a housing having a wall defining one, or more than one chamber, the wall made of a light-scattering and light-reflecting material selected from the group consisting of Teflon®, Teflon®-PTFE, Teflon®-PTFE with 25% glass fibers, and Fluorosint™, the housing configured in the shape of a body part.

20. The artificial member of claim 19, wherein the body part is selected from the group consisting of a finger, a lip, an earlobe, a pinch of skin, a web of a hand, and a web between toes.

21. The artificial member of claim 19, wherein the one or more than one chamber is filled with air, water, O-cellulose material, or a gel material containing Amaranth, sodium benzoate and reflective particles, or a combination thereof, the reflective particles comprising Teflon®-PTFE, Titanium Dioxide (TiO$_2$) or polystyrene nanospheres.

22. The artificial member of claim 19, wherein the wall of the housing is solid.

23. The artificial member of claim 19, wherein the wall of the housing defines two, or more than two chambers.

24. The artificial member of claim 19, wherein the wall of the housing defines two chambers.

25. The artificial member of claim 19, wherein the housing defines a first and a second end, wherein the first and the second end are sealed.

26. A method for verifying the precision and accuracy of a non-invasive monitoring device comprising:
    a) inserting an artificial member into a measuring receptor, the measuring receptor operatively connected to the non-invasive monitoring device, the artificial member comprising a housing having a wall defining one, or more than one chamber, the wall made of a light-scattering and light-reflecting material selected from the group consisting of Teflon®, Teflon®-PTFE, Teflon®-PTFE with 25% glass fibers, and Fluorosint™, the housing configured in the shape of a body part;

b) measuring the absorbance spectrum of the artificial member; and c) comparing the absorbance spectrum of the artificial member with an absorbance spectrum obtained from the body part, thereby verifying the precision and accuracy of the non-invasive monitoring device.

27. The method of claim 26, wherein the body part is selected from the group consisting of a finger, a lip, an earlobe, a pinch of skin, a web of a hand, and a web between toes.

28. The method of claim 26, wherein the one or more than one chamber is filled with air, water, O-cellulose material, or a gel material containing Amaranth, sodium benzoate and reflective particles, or a combination thereof, the reflective particles comprising Teflon®-PTFE, Titanium Dioxide ($TiO_2$) or polystyrene nanospheres.

* * * * *